US006142973A

United States Patent [19]

Carleton et al.

[11] Patent Number: 6,142,973

[45] Date of Patent: Nov. 7, 2000

[54] BALLOON CATHETER FOR REPAIRING BIFURCATED VESSELS

[75] Inventors: Maria Carleton, Galway; Shane MacNally, Dublin; Geraldine Standish, Ballybrit, all of Ireland

[73] Assignee: AVE Connaught, Dublin, Ireland

[21] Appl. No.: 09/187,616

[22] Filed: Nov. 6, 1998

Related U.S. Application Data

[60] Provisional application No. 60/064,913, Nov. 7, 1997.

[51] Int. Cl.[7] .................................................. A61M 29/00

[52] U.S. Cl. ................................ 604/96; 604/96; 604/915

[58] Field of Search .................... 604/96, 101, 915–919; 606/191, 194

[56] References Cited

U.S. PATENT DOCUMENTS

| | | | |
|---|---|---|---|
| 4,413,989 | 11/1983 | Schjeldahl et al. . | |
| 5,403,340 | 4/1995 | Wang et al. . | |
| 5,613,980 | 3/1997 | Chauhan . | |
| 5,669,924 | 9/1997 | Staknovich | 606/108 |
| 5,720,735 | 2/1998 | Dorros | 604/284 |

FOREIGN PATENT DOCUMENTS

| | | |
|---|---|---|
| 96/39970 | 12/1996 | WIPO . |
| 96/40347 | 12/1996 | WIPO . |
| 97/16217 | 5/1997 | WIPO . |

*Primary Examiner*—Wynn Wood Coggins
*Assistant Examiner*—Kevin C. Sirmons
*Attorney, Agent, or Firm*—Sterne, Kessler, Goldstein & Fox PLLC

[57] ABSTRACT

A balloon catheter comprising a body and first and second arms attached to one end of the body. A common inflation lumen extends along the body and branches into each of the arms. An expandable balloon is provided on each arm so as to be in fluid communication with the lumen of each arm. The catheter further includes a guide wire lumen in each of the arms. A method for dilating a narrowed bifurcated vessel is also disclosed.

17 Claims, 6 Drawing Sheets

10 41 28 32 18 38 12 14 16 40 30 34 20 42

16
12
38
40

34
32
20
18
28
30

68
70
54
52
50

56
66
72
60
74
58
62
64

82
84
80
88
90
92
94
96
98
100

114

112
110
116
118
120
122
123
126
130
128

DUAL BALLOON DELIVERY SYSTEM

BALLOON CATHETER FOR REPAIRING BIFURCATED VESSELS

RELATED U.S. APPLICATION(S)

The present application claims priority from U.S. Provisional Application No. 60/064,913, filed Nov. 7, 1997 which is hereby incorporated herein by reference.

TECHNICAL FIELD

The present invention relates to medical devices and procedures and, more particularly, to catheter systems and methods for dilating obstructed portions of a patient's vasculature.

BACKGROUND ART

Balloon angioplasty employs balloon tipped catheters to expand the walls of narrowed arteries and to deploy endoluminal prostheses to maintain lumen patency. Although systems and techniques exits that work well in many cases, no technique is applicable to every case. For example, special methods exist for dilating lesions that occur in branched vessels. These methods seek to prevent the collapsing or obstructing of neighboring vessels during the dilation of other vessels. Such methods include techniques for using double guide wires and sequential percutaneous transluminal coronary angioplasty (PTCA) with stenting or the "kissing balloon" and "kissing stent" technique, which provide side branch protection. Although these methods can work well, they often require the control of multiple balloon catheters, which can be difficult for the treating physician. Moreover, the systems employed during these techniques generally have a static design making it difficult to tailor the device to the individual requirements of the patient. For example it can be difficult to tailor the size and the length of the balloon and or the over-the-wire length suited to the location of the target vessels.

SUMMARY OF THE INVENTION

The invention provides, inter alia, a balloon angioplasty catheter comprising a common inflation lumen and two guide wire lumens to allow angioplasty and stent deployment in branched or bifurcated arteries. The guide wire lumens permit the location of wires in the main and side branch arteries.

In one embodiment of the invention, the catheter includes an inflation lumen with two guide wire lumens, based on a rapid exchange or monorail design.

The proximal section of the catheter is an inflation lumen which transitions to two co-axial distal sections. The distal sections are comprised of two tubes, connected to an expandable balloon at the end of the catheter, the inner tube allows the passage of a guide wire and is typically made from a low friction material, the outer lumen is a continuation of the inflation lumen. The guide wire enters the catheter at a port approximately 10 to 30 cm proximal to the balloon and exits at the tip of the balloon.

Another embodiment of the invention is based on an over-the-wire design, where the guide wire lumen(s) extend the length of the catheter and beyond one or both of the balloons. This embodiment could be used to address a possible complication that occurs when multiple guide wires are used, that is wire tangling prior to the branched vessel. In this instance, the guide wire(s) would be encapsulated for the length of the catheter reducing the possibility of tangling of the wires.

Another embodiment of the invention is based on a fixed wire design, where the guide wire is incorporated as part of the catheter.

Another embodiment of the invention has an extra sleeve over the endoluminal prostheses, which may provide benefits, including improved trackability and efficiency of the device and additional security of the stent on the balloon.

The dual balloon delivery system disclosed herein may be used for the dilation of obstructed areas of a patient's vasculature as well as for the delivery of self-expanding and non-self-expanding stents. U.S. patent application Ser. No. 08/937,199 describes an endoluminal prostheses that can be placed at a bifurcated region. Moreover, the system may be employed to deploy multiple stents in a single procedure and may be used in conjunction with, for example, an embolic filter.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIG. 1A is an enlarged view of a bifurcated joint 16 shown in FIG. 1.

DETAILED DESCRIPTION OF SPECIFIC EMBODIMENTS

The invention will now be described with reference to certain illustrated embodiments and certain exemplary practices. Specifically, the invention will be described hereinafter in connection with PTCA medical procedures. However, it should be understood that the following description is only meant to be illustrative of the invention and is not meant to limit the scope of the invention which is applicable to other medical procedures including PTCA, as well as procedures for delivering stents and stent-grafts, particularly bifurcated stents, and any other catheter-based medical procedure in which a dual catheter delivery device is beneficial.

Figure 1:
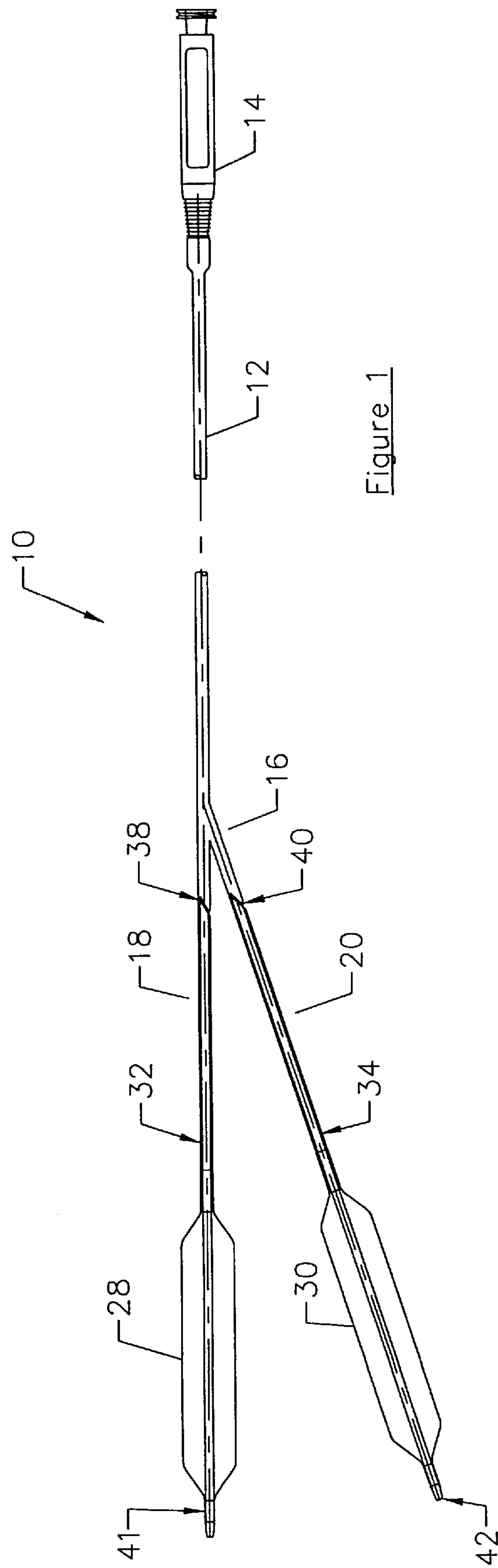
FIG. 1 illustrates one embodiment of the balloon catheter of the present invention.
Figure 1:
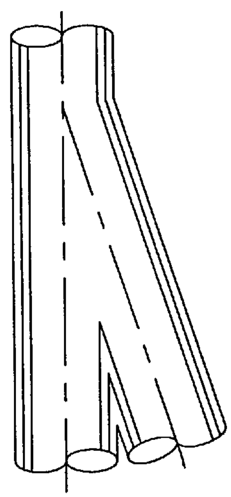

FIG. 1 depicts one catheter 10 that includes a main body 12, a hub 14, a joint 16, an arm 18, an arm 20 and balloons 28 and 30.

The catheter 10 depicted in FIG. 1 is a dual balloon catheter system that includes the main body 12 that has a proximal end and a distal end wherein the proximal end couples to the hub 14 and the distal end couples to the joint 16. The main body 12 has an interior lumen that extends through the entirety of the main body 12 and couples the hub 14 into fluid communication with the joint 16. The main body 12 can comprise a thin wall made from a metal, a polymer, or other material. The joint 16, as seen in FIG. 1A, includes a partition that directs fluid flowing from the interior lumen of the main body 12 into a pair of lumens (not shown) each of which extends through one of arms 18 or 20. As further shown by FIG. 1, the balloons 28 and 30 are positioned on respective one of the arms 18 and 20. The interior of each of the balloons 28 and 30 preferably, is in fluid communication with the respective one of the lumens that extend through the arms 18 and 20. In this way, the interior of each of the balloons 28 and 30 is permitted to be in fluid communication with arms 18 and 20, respectively. The lumens, as can be appreciated, provides the fluid passages (not shown) extending through the hub 14, main body 12, joint 16 and arms 18 and 20 to carry fluid from an external fluid source to the interior of the balloons 28 and 30. Accordingly, the hub 14 can be coupled to a source of fluid pressure which can introduce a fluid, typically a dilute contrast solution, into the hub 14 to travel along the lumens into the interior of the balloons 28 and 30 to inflate each of the balloons. The balloons 28 and 30, although shown on only a portion of the arms 18 and 20, may be designed, in certain embodiments, to extend substantially along the entire length of the arms 18 and 20. The distance between the proximal end of each balloon and the joint 16 may be varied according to manufacturing specifications. The distance preferably ranges from about 1 cm to about 30 cm.

The catheter 10 depicted in FIG. 1 further includes guide wire lumens 32 and 34 each of which travels through a respective one of the arms 18 and 20. In this depicted embodiment, each of the guide wire lumens 32 and 34 terminates at a respective guide wire port 38 and 40 that extends through the wall of the respective arm 18 or 20 to permit the guide wire lumen to communicate with the environment exterior to the catheter 10. Consequently, each of the guide wire lumens 32 and 34 also includes openings 41 and 42, respectively, disposed at the distal end of each of the arms 18 and 20. Accordingly, each arm 18 and 20 of the catheter 10 can be fed over a guide wire, such that each guide wire extends through a respective one of the distal openings 41 and 42 to the guide wire lumen and exits from the guide wire lumen at the respective guide wire port 38 and 40.

Figure 2:
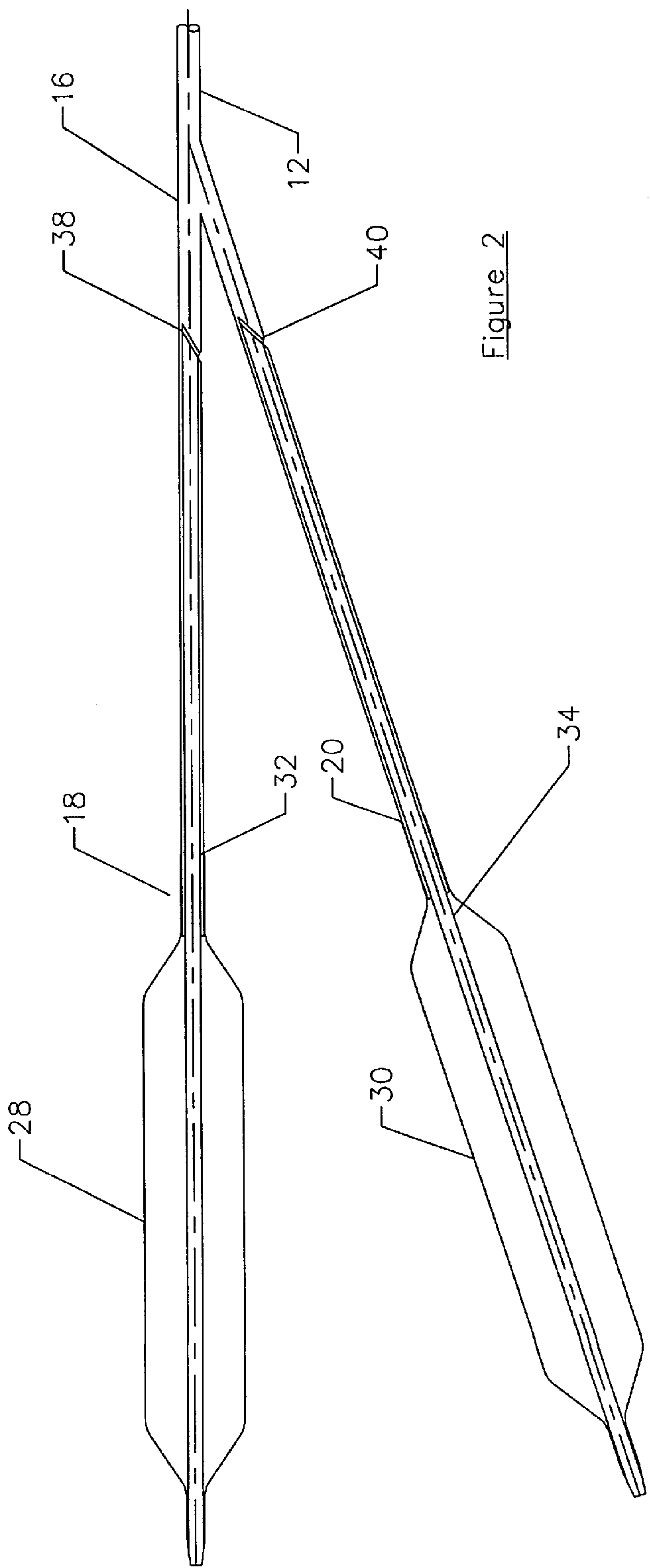
FIG. 2 is an enlarged drawing of the distal portion of the catheter of FIG. 1.

FIG. 2 depicts in greater detail the structure of the arms 18 and 20. In particular, FIG. 2 shows that the main body 12 includes an interior lumen that bifurcates at joint 16 and extends into each of the arms 18 and 20. The main body 12, as well as each of the arms 18 and 20, can be hollow tubular members of the type capable of carrying a fluid, such as pressured saline. As depicted in FIG. 2, at a location distal to the joint 16, each of the arms 18 and 20 has a guide wire port 38 or 40, which provides an opening into a guide wire lumen that extends co-axially with the arm, and within which the guide wire lumen may be disposed. The interior structure of each arm 18 and 20 of the catheter 10 are similarly constructed and for clarity, only the structure of arm 18 will be described. Balloon 28 is mounted above the periphery of the arm 18 to form a fluid-tight seal that prevents fluid from leaking between the balloon 28 and the arm 18. As further shown in FIG. 2, the guide wire lumen 32 continues past the proximal end of the balloon 28 and extends to the distal most portion of the catheter 10. At this distal most portion, the balloon 28 joins with the guide wire lumen to form a fluid-tight seal that prevents fluid from leaking between the balloon 28 and the guide wire lumen 32. The guide wire lumen 32 terminates at an opening that allows a guide wire to pass into the guide wire lumen 32. As further shown by FIG. 2, the guide wire lumen 32 is sufficiently radially smaller than the arm 18 to thereby provide an angular space between the guide wire lumen 12 and the wall of the arm 18 through which an inflation fluid can pass for inflating the balloon 28.

In one embodiment of the invention, the joint 16 can be formed of a flexible tubing to provide a resilient structure that allows for the transverse movement of the arms 18 and 20. The arms 18 and 20 can be formed of a flexible, resilient, biocompatible material suitable for disposition within the vascular system of a patient. To provide additional strength to the arms 18 and 20, each arm may include a strong polymer along its outer surface. Alternatively, each arm may include a stiffening wire within the inflation lumen to provide additional support for the arm. The stiffening wire may extend from about 1 cm distal of the joint 16 up to the distal end of the balloon. In a further embodiment, one arm may included the strong polymer and the other arm may include the stiffening wire.

The balloons can be made of a compliant or non-compliant material, and can be adapted to perfuse a therapeutic agent or other material. Further, the balloons can have a tapered design to suit variations in vessel diameter and can be of different sizes for vessels of different diameters. More than two arms can be carried at the distal end of the device to allow for more than two vessels to receive balloons.

Optionally, the arms 18 and 20 extending from the joint 16 can be removably mounted to the joint 16, such that each arm can be detached from the joint 16 and replaced with an alternative arm design or size. The arms can be inserted into the joint 16 to form a snap fit (not shown) that is sufficiently strong to allow the arms of the catheter to slide along a guide catheter without detaching from the joint. Alternative connecting techniques can be employed for coupling the arms to the joint 16 without departing from the scope of the invention. The ability to mount arms of various sizes allows the treating physician to select alternate lengths and designs for the arms employed during the angioplasty operation. The joint 16 can also include a valve to control the flow of fluid to one of the inflation ports of the balloons to allow staggered inflation of the balloons. The valve could also be located at alternate positions.

In a further optional embodiment, the arms 18 and 20, as well as the main body 12, can be coated, either in whole or in part, with a pharmaceutical substance suitable for enhancing the delivery of a stent, or for carrying a therapeutic agent to the site of a lesion. Additionally, the arms and body can be coated with a material that enhances the lubricity of the device, to facilitate the sliding of the device through a guide catheter.

Figure 3:
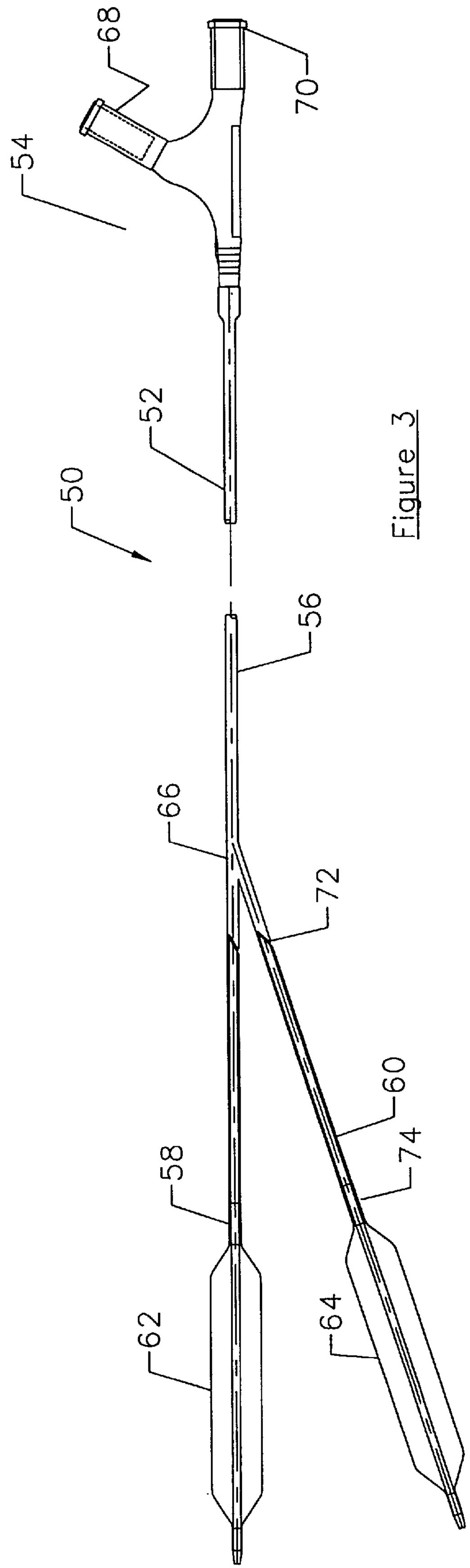
FIG. 3 depicts a combined rapid exchange and over-the-wire embodiment.

FIG. 3 depicts a further embodiment of the invention. Specifically, FIG. 3 depicts a catheter 50 that includes a main body 52, a hub 54, and over-the-wire guide wire lumen 56, an arm 58, arm 60, balloons 62 and 64, joint 66, inflation port 68, guide wire port 70, and arm guide wire port 72.

The catheter 50 depicted in FIG. 3 comprises both a rapid exchange and an over-the-wire catheter design. As shown in FIG. 3, the main body 52 has a proximal end that connects to the hub 54 which includes an inflation port 68 and a guide wire port 70. The main body 52 couples at its distal end to the joint 66 which, in turn, couples to arm 58 and arm 60. FIG. 3 further illustrates that a guide wire lumen 56 extending through the main body 52 and continuing on through the arm 58 and through the balloon 62 terminating at a port at the distal most end of the arm 58. Accordingly, the depicted guide wire lumen 56 provides a continuous lumen that extends from the distal most portion of the arm 58 to the guide wire port 70. FIG. 3 further illustrates arm 60 having a shortened guide wire lumen 74 that extends from the guide wire port 72 through the arm 60, through the balloon 64 and terminates at the distal most portion of the arm 60. The guide wire lumen 74 provides a rapid exchange guide wire lumen through which a guide wire may be maneuvered through the arm 60 to permit the arm 60 to be delivered into a patient's body.

Figure 4:
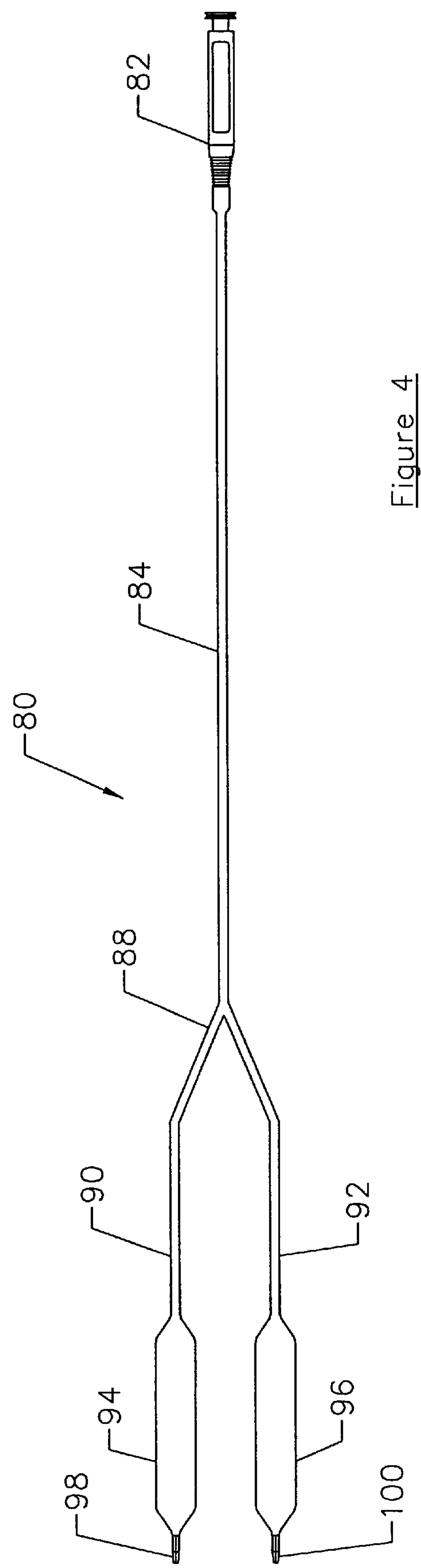
FIG. 4 depicts a fixed guide wire embodiment.

FIG. 4 illustrates a further embodiment of the invention, specifically, a catheter 80 having fixed guide wires, each of which is mounted at a distal end of one of the two balloons carried by the catheter 80.

The catheter 80 includes a luer lock 82, a main elongate body 84, a joint 88, a first arm 90, a second arm 92, a first balloon 94, a second balloon 96, a fixed guide wire 98 and a fixed guide wire 100.

As illustrated in FIG. 4, the luer lock 82 is coupled to a proximal end of the main elongate body 84. The luer lock 82 can be a conventional luer lock that provides a coupling for placing a lumen within the main elongate body 84 into fluid communication with a fluid source. The main elongate body 84 includes an interior lumen that can act as an inflation lumen for carrying an inflation fluid from the luer lock 82 through the joint 88. The main elongate body 84 can be formed of a flexible biocompatible material suitable for acting as a catheter that can be inserted in to the vascular system of a patient. The length of the main elongate body 84 can be selected according to the application, and in one embodiment, the main elongate body 84 is sized for application during a PTCA procedure and is approximately 150 cm to 300 cm in length.

The joint 88 depicted in FIG. 4 is carried at the distal end of the body 84, and inbody 84, and includes two distal branches that bifurcate body 84 into two separate inflation lumens each of which is carried within one respective arm 90 or 92. A joint 88 can be formed of a flexible tubing to provide a resilient structure that allows for the transverse movement of the arms 90 and 92. The arms 90 and 92 can be formed of a flexible, resilient, biocompatible material suitable for disposition within the vascular system of a patient.

Each of the depicted balloons 94 and 96 couples into fluid communication with one of the respective inflation lumens that travels through each of the arms 90 and 92. For example, the interior of balloon 94 couples into fluid communication with the inflation lumen extending through the arm 90. The depicted balloons 94 and 96 can be any balloons suitable for dilating an obstructed vessel and can have dimensions selected for the particular vessel being treated.

FIG. 4 further depicts that fixed wires 98 and 100 are positioned at the distal most ends of the inflation lumens extending through the arms 94 and 96. Optionally, the fixed guide wires 98 and 100 can extend from the distal most end of the balloons 94 and 96. It will be apparent to one of ordinary skill in the art that other configurations for providing the catheter 80 with fixed guide wires can be practiced with the present invention without departing from the scope thereof. Each of the fixed guide wires 98 and 100 can be formed of a flexible wire material suitable for being inserted through a lesion within a vessel. Each guide wire 98 and 100 can be made of a stainless steel wire dimensionally adapted for fitting through the stenosed area of a vessel being treated by a PTCA procedure. Other suitable materials can be employed for forming the guide wires 98 and 100 without departing from the scope of the invention.

In an alternate embodiment of the catheter 80 depicted in FIG. 4, one of the arms 90 or 92 can be provided with a guide wire lumen that extends through the arm, through the balloon, and terminates at a guide wire port located at the distal most end of the respective balloon. No fixed wire would be attached to the arm having a guide wire lumen. Instead, the treating physician could feed a guide wire through the guide wire lumen, either by passing a guide wire through a guide wire port located at the proximal end of the arm or by feeding a guide wire through a guide wire lumen extending through the main elongate body 84, through the joint 88 and into the guide wire lumen of the arm. This alternate embodiment provides a catheter having a combined fixed guide wire arm and over the wire, or rapid exchange, catheter.

Figure 5:
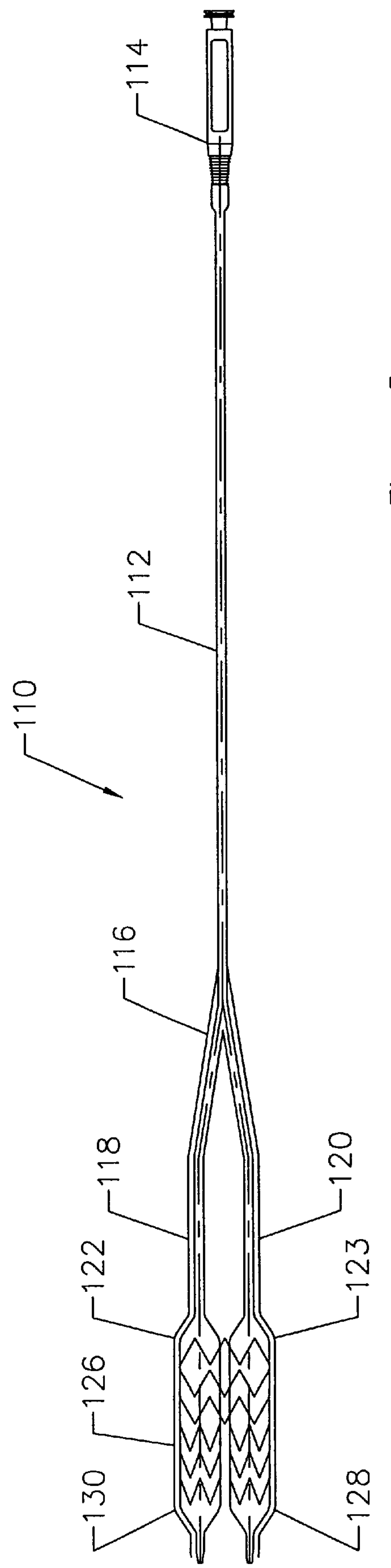
FIG. 5 illustrates a catheter with an integral sleeve over the balloon and stent.

FIG. 5 illustrates another embodiment of the invention. Specifically, a catheter 110 is shown to include a main elongate body 112, a luer lock 114, a joint 116, and arm 118, a second arm 120, a balloon 122, and a balloon 123, a sleeve 126, and stents 130 and 128.

In the catheter 110 of FIG. 5, the stents and balloons are covered with a sleeve 126 that acts to facilitate the retraction of the balloons and stents into the interior lumen of the catheter from which the dual balloon catheter is deployed. The sleeve 126 can be formed of an elastic material provided on the surface of the two arms which acts to hold the stents 128 and 130 position on the balloons during delivery of the balloons through the guide catheter. Moreover, the depicted sleeve 126 holds the stents 128 and 130 with sufficient force to prevent the stents from sliding off the balloons 122 and 124 during the retraction of the catheter 110 within the interior of the guide catheter. Although FIG. 5 depicts a dual balloon catheter 110 that includes two separate stents 128 and 130, it will be apparent to one of ordinary skill in the art that the sleeve 126 can be employed for holding a single body bifurcated stent in place over the dual balloon system. Similarly, it will be apparent to one of ordinary skill in the art that the sleeve 126 can be employed with a dual balloon delivery system which is not delivering stents to the site of the lesions but is inserting balloons at the site of the lesion for dilating obstructed vessels.

In one embodiment, the sleeve 126 extends from the distal end of the balloons 122 and 123, through the arms 118 and 120 through joint 116 and through the main elongate body 112. Accordingly, the sleeve 126 extends through the interior lumens of the catheter 110 to provide at the proximal end, typically by the luer lock 114, a portion of the sleeve that can be gripped by the treating physician. This allows the treating physician to grip the sleeve 126 and extract it proximally from the interior lumens of the catheter 110 thereby releasing the arms 118 and 120, as well as the balloons 122 and 123, so that the balloons can be dilated to position the stents within the lesions or lesion being treated. The portion of the sleeve extending through the main elongate body may be, in an embodiment, strands of thread to avoid being too bulky within the interior of the body 112. In another embodiment of the invention, the sleeve 126 may extend through the arms and terminate within the joint 116. In this embodiment, a pair of wires may extend from the sleeve 126 through the main body to the luer lock 114 to permit the physician to extract the sleeve from the interior lumens of the catheter 110. In a further embodiment, the sleeve 126 may extend from the distal end of the balloons 122 and 123 over the arms 128 and 120, over the joint 116, and over the main elongate body 112 to the luer lock 114. This embodiment simply permits the physician to pull on the portion of the sleeve 126 near the luer lock 114 to release the arms and the balloons. The sleeve 126 may extend, in an alternate embodiment, to over the joint 116, and include a pair of wires attached to the sleeve to permit the sleeve 126 to be pulled proximally.

Figure 6:
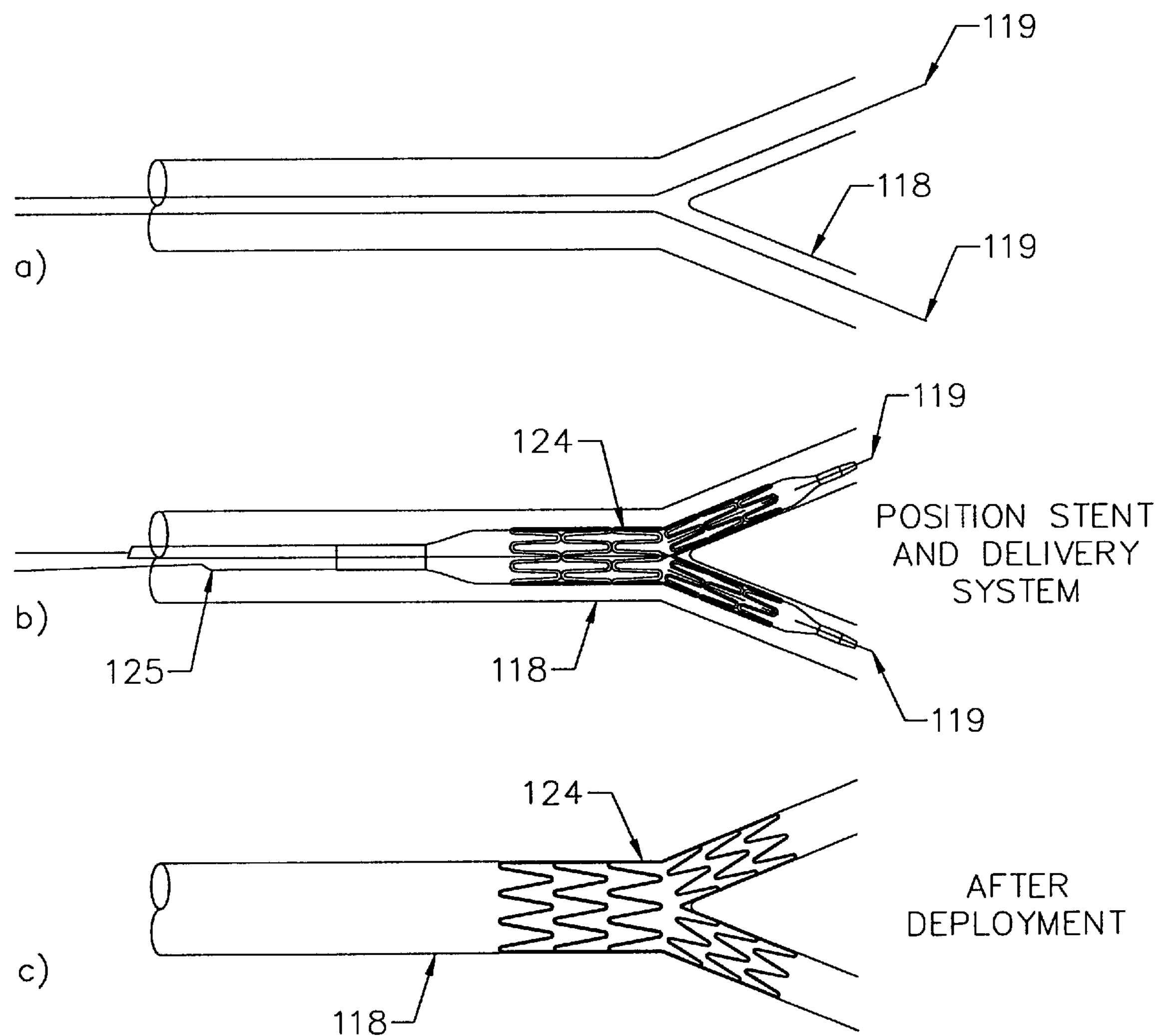
FIG. 6 illustrates one proposed method of stent deployment.

FIG. 6 illustrates one possible method to deploy a stent, shown here as general outline 124 to simplify the diagram and aid viewing. Two guide wires 119 are positioned in the bifurcate vessel 118 by any suitable means of the prior art, as illustrated in FIG. 6(*a*). The bifurcated stent 124, is crimped onto the balloons 125 to obtain a low profile state. Preferable, the stent 124 has a length which is substantially equivalent to or less than the length of the balloon. In this manner, the balloons 125 will be able to inflate the arms of the stent as well as the body of the stent 124. The two balloons 125 of the dual balloon catheter with the crimped stent 124 are advanced over the guide wires 119 to the bifurcated vessel, as depicted in FIG. 6(*b*). Advancement of the catheter will be limited by the bifurcated stent 124 when the arms of stent have entered into the respective branches of the vessel. The system can be advanced through a guiding catheter (not shown) to the site of the bifurcated vessel by the prior known art. The dual balloon catheter is now employed to expand the stent to its deployed configuration by applying a radial force on the modules of the stent by means of the two balloons 125, as depicted in FIG. 6(*c*). Since both balloons extend from the arms of the stent to the body of the stent, the entire stent may be inflated radially. The balloons 125 are deflated and can be removed along with the guide wires to leave the stent 124 in the deployed configuration. Additional post dilatation may follow stent deployment, if so required.

The dual balloon catheter may also be used, in the manner described above, to dilate a narrowed or bifurcated vessel without using a stent. A stent, as can be appreciated, may only be necessary if there is a likelihood of restenosis at the obstruction site and maintenance of luminal patency is desired.

It should be understood that the foregoing description of the invention is intended merely to be illustrative thereof and that other embodiments, modifications and equivalents will be apparent to those skilled in the art without departing from its principles. It shall also be understood that the word "a" as used herein shall not be understood to mean "only one" and instead shall be understood to mean "at least one".

We claim:

1. A balloon catheter, comprising an elongate main body having a proximal end and a distal end and a main lumen extending there through, a joint coupled to the distal end of the elongate body and having a partition for dividing the main lumen into at least first and second fluid passages first and second arms, each coupled to the joint and each having an interior lumen in fluid communication with a respective one of first and second passages; and a balloon mounted on each arm at a location that is distal of the joint.

2. A balloon catheter according to claim 1, wherein at least one of the first and second arms includes a guide wire lumen which terminates in a guide wire exit port at a location distal to the joint for allowing rapid exchange of a guide wire.

3. A balloon catheter according to claim 1, further including a guide wire lumen extending through the main body, the joint and at least one of the first and second arms.

4. A balloon catheter according to claim 1, wherein the joint includes a partition for dividing the main lumen into at least a first passage, a second passage, and a third passage.

5. A balloon catheter according to claim 1, further including a guide wire fixedly attached to at least one of the first and second arms at an end distal to the joint.

6. A balloon catheter according to claim 1, further including a sleeve mounted about one of the balloons.

7. A balloon catheter according to claim 1, wherein at least one of the balloons comprises a non-compliant material.

8. A balloon catheter according to claim 1, further including a coating of a pharmaceutical substance.

9. A balloon catheter according to claim 1, further including a coating of a substrate for enhancing lubricity of the catheter.

10. A balloon catheter according to claim 1, further including means for restricting a flow of fluid through the lumen of at least one of the arms to provide staggered inflation of the balloons.

11. A balloon catheter according to claim 1, wherein the balloons are offset, staggered, to expand a bifurcated vessel within which the balloons are positioned to different diameters.

12. A balloon catheter of claim 1, where each balloon is tapered to suit the variation in vessel diameter.

13. A balloon catheter of claim 1, where the balloons have a perfusion capability.

14. A method for dilating an obstruction in a bifurcated vessel and delivering a stent, the method comprising:

providing a balloon catheter having a main body with a main lumen extending therethrough, a joint coupled to one end of the main body having a partition for dividing the main lumen into first and second fluid passages, and first and second arms coupled to the joint, each arm having a respective one of said first and second fluid passages and a guide wire lumen extending therethrough and first and second balloons mounted on respective ones of said first and second arms at a position distal to the joint;

positioning a bifurcated stent onto the first and second balloons;

placing a guide wire in each branch of the bifurcated vessel;

advancing each of said first and second arms over guide wires, so as to move each guide wire into the guide wire lumen of each arm;

maneuvering the catheter along the vessel to the obstruction, so as to position each of said first and second balloons within a branch of the bifurcated vessel; and expanding each balloon, so as to expand the bifurcated stent against the vessel.

15. A method as set forth in claim 14 further including the steps of:

deflating the balloon; and removing the catheter from the vessel, while leaving the stent in position.

16. A method for dilating an obstruction in a bifurcated vessel, the method comprising:

providing a balloon catheter having a main body with a main lumen extending therethrough, a joint coupled to one end of the main body having a partition for dividing the main lumen into first and second fluid passages, and first and second arms coupled to the joint, each arm having a respective one of said first and second fluid passages and a guide wire lumen extending therethrough and first and second balloons mounted on respective ones of said first and second arms at a position distal to the joint;

placing a guide wire in each branch of the bifurcated vessel;

advancing each arm over a guide wire, so as to move each guide wire into the guide wire lumen of each arm;

maneuvering the catheter along the bifurcated vessel to the obstruction, so as to position each balloon within a branch of the bifurcated vessel; and expanding each balloon with the bifurcated vessel.

17. A method as set forth in claim 16 further including the steps of:

deflating the balloon; and removing the catheter from the vessel.

* * * * *

UNITED STATES PATENT AND TRADEMARK OFFICE

CERTIFICATE OF CORRECTION

PATENT NO. : 6,142,973
DATED : November 7, 2000
INVENTOR(S) : Carleton et al.

It is certified that error appears in the above-identified patent and that said Letters Patent is hereby corrected as shown below:

Column 5,
Line 29, insert -- main elongate -- after "the";
Line 29, delete "and inbody 84,";
Line 30, insert -- the main lumen of the main elongate -- after "bifurcate";

Claims,
Please correct as follows:

1. A balloon catheter, comprising:
an elongate main body having a proximal end and a distal end and a main lumen extending there through [,];
a joint coupled to distal end of the elongate body and having a partition for dividing the main lumen into [at least] first and second fluid passages;
first and second arms, each coupled to the joint and [each having an interior lumen] in fluid communication with respective one of said first and second fluid passages; and
[a balloon] first and second balloons, each mounted on a respective one of said first and second arms [each arm] at a location that is distal of the joint, wherein each of said first and second balloons is in fluid communication with a respective one of said first and second fluid passages.

4. A balloon catheter according to claim 1, wherein the joint includes a partition for dividing the main lumen into at a least a first fluid passage, a second fluid passage, and a third fluid passage.

6. A balloon catheter according to claim 1, further including a sleeve mounted about at least one of the first and second balloons.

7. A balloon catheter according to claim 1, wherein at least one of the first and second balloons comprises a non-compliant material.

10. A balloon catheter according to claim 1, further including means for restricting a flow of fluid through the lumen of at least one of the first and second arms to provide staggered inflation of the balloons.

11. A balloon catheter according to cliam 1, wherein the first and second balloons are offset[,] and staggered to expand a bifurcated vessel within which the first and second balloons are positioned to different diameters.

UNITED STATES PATENT AND TRADEMARK OFFICE
CERTIFICATE OF CORRECTION

PATENT NO. : 6,142,973
DATED : November 7, 2000
INVENTOR(S) : Carleton et al.

It is certified that error appears in the above-identified patent and that said Letters Patent is hereby corrected as shown below:

12. A balloon catheter according to [of] claim 1, wherein [where] each of said first and second balloons [balloon] is tapered to suit the variation in vessel diameter.

13. A balloon catheter according to [of ] claim 1, wherein said first and second [where the] balloons have a perfusion capability.

15. A method as set forth in claim, 14, further including the steps of:
deflating each of said first and second balloons [the balloon]; and
removing the catheter from the bifurcated vessel, while leaving the bifurcated stent in position.

Column 8, claim 16,
Line 61, delete "with" and insert -- within --;

17. A method as set forth in claim 16, further including the steps of:
deflating each of said first and second balloons [the balloon]; and
removing the catheter from the bifurcated vessel.

Signed and Sealed this

Twenty-third Day of October, 2001

Attest:

*Nicholas P. Godici*

NICHOLAS P. GODICI

*Attesting Officer* *Acting Director of the United States Patent and Trademark Office*